United States Patent [19]

Heifetz et al.

[11] Patent Number: 4,751,229

[45] Date of Patent: Jun. 14, 1988

[54] TREATING FUNGAL INFECTIONS WITH SUBSTITUTED-(6-(TETRAHYDRO-4-HYDROXY-2-OXO-2H-PYRAN-2-YL)E-THYL)- OR ETHENYL)PYRAZOLES

[75] Inventors: Carl L. Heifetz; Milton L. Hoefle; Bruce D. Roth, all of Ann Arbor; Drago R. Sliskovic, Ypsilanti, all of Mich.; Michael W. Wilson, Waukegan, Ill.

[73] Assignee: Warner-Lambert Company, Morris Plains, N.J.

[21] Appl. No.: 71,672

[22] Filed: Jul. 9, 1987

[51] Int. Cl.[4] ............................................. A01N 43/56

[52] U.S. Cl. ..................................... 514/406; 548/374; 548/378

[58] Field of Search ................. 514/406; 548/374, 378

[56] References Cited

U.S. PATENT DOCUMENTS 4,613,610  9/1986  Wareing ............................. 514/406

Primary Examiner—Richard A. Schwartz
Assistant Examiner—Kurt G. Briscoe
Attorney, Agent, or Firm—Jerry F. Janssen

[57] ABSTRACT

A method of treating fungal infections in mammals employing 1,3,5-trisubstituted-4- (4-hydroxy-2-oxopyran-6-yl)pyrazoles is disclosed.

5 Claims, No Drawings

TREATING FUNGAL INFECTIONS WITH SUBSTITUTED-(6-(TETRAHYDRO-4-HYDROXY-2-OXO-2H-PYRAN-2-YL)ETHYL)- OR ETHENYL)PYRAZOLES

BACKGROUND OF THE INVENTION

The present invention relates to medical methods of treatment. More particularly, it is concerned with a method of treating fungal infections in a mammal employing certain substituted-4-[6-(tetrahydro-4-hydroxy-2-oxo-2H-pyran-2-yl)ethyl]- and -ethenyl]pyrazoles and the corresponding ring-opened β,δ-dihydroxy-heptanoic and heptenoic acids derived therefrom.

U.S. Pat. No. 4,613,610 to Wareing discloses certain substituted (6-tetrahydro-4-hydroxy-2-oxo-2H-pyran-2-yl)alkyl]pyrazoles and their use as agents for inhibiting cholesterol biosynthesis and lowering blood cholesterol levels.

The past decade has been quite productive in the discovery of new antibacterial agents. Most of the new agents have been parenteral agents, with the improved activity primarily in the gram-negative component of the antibacterial spectrum.

However, there has not been corresponding development in the area of antifungal agents. The increasing efficacy and potency of antibacterial therapy seems to have created an ecologic niche that has been filled by superinfecting fungal pathogens. Yet, no new types of antifungal agents have appeared which offer promise in the treatment of the important systemicmycoses which occur in immunosuppressed hosts.

A number of potent antimicrobial compounds are available for the treatment of acute disease, but therapy for chronic infections is often frustrating. The development of antibacterial compounds that could be safely administered via the oral route for a long period (as in an outpatient setting) might make a major difference in the management of these chronic infections. Oral medications active against staphylococci, gram-negative rods, and fungi would make it possible for patients to be discharged earlier, or even to be managed without hospitalization.

SUMMARY OF THE INVENTION

In accordance with the present invention, there is provided a method of treating fungal infections in a mammal comprising administering certain 3- or 5-(substituted-phenyl)-4-[6-(tetra-hydro-4-hydroxy-2-oxo-2H-pyran-2-yl)ethyl]and 3- or 5-(substituted-phenyl)-4-[6-(tetrahydro-4-hydroxy-2-oxo-2H-pyran2-yl)-ethenyl]-pyrazoles or a corresponding ring-opened β,δ-dihydroxyheptanoic or -heptenoic acid derived therefrom by the opening of the lactone ring.

In particular, the present invention provides a method of treatment employing compounds of structural Formula 1:

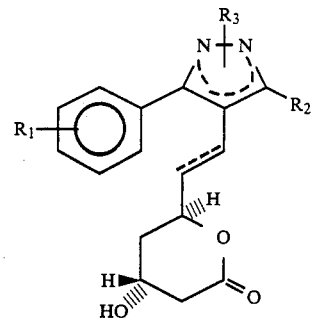

where the dashed lines indicate single or double bonds; where $R_1$ is hydrogen; halogen; straight or branched lower alkyl; hydroxy; straight or branched lower alkyloxy; or straight or branched lower alkanoyl; $R_2$ is straight or branched lower alkyl; or trifluoromethyl; $R_3$ is phenyl; benzyl; or phenyl substituted with halogen, hydroxy, nitro, amino, straight or branched lower alkyl, straight or branched lower alkyloxy, methylsulfonyl, methylsulfinyl, acetamido, or benzoyl; and the pharmaceutically salts thereof.

Also contemplated as falling within the scope of the invention is the use of the ring-opened β,δ-dihydroxy acids of Formula 2:

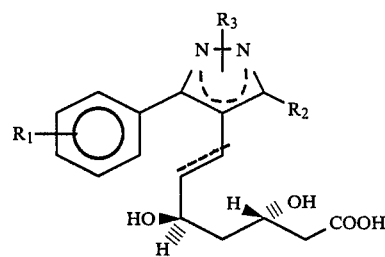

where the dashed lines, $R_1$, $R_2$, and $R_3$ are as previously defined, and the pharmaceutically acceptable salts thereof.

DETAILED DESCRIPTION Compounds for use in the method of this invention possess structural Formula 1:

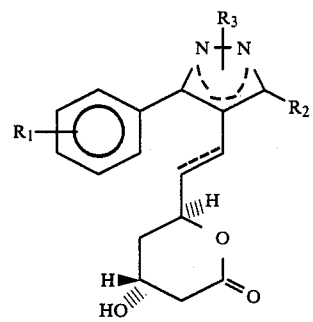

where the dashed lines represent single or double bonds.

The dashed lines in the pyrazole group are meant to indicate single or double bonds, depending upon the position of attachment of the $R_3$ substituent group to the pyrazole ring. For example, when $R_3$ is attached to the nitrogen atom adjacent ot the substituted phenyl group, the arrangement of double bonds in the pyrazole ring is that shown in structural Forumula 1a:

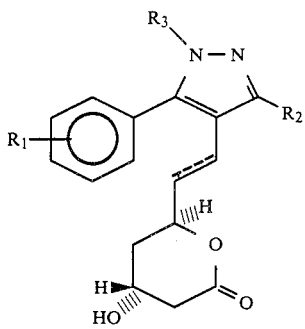

Alternatively, when the substituent agroup R₃ is attached to the nitrogen atom adajcent to substitutent group R₂, the arrangement of double bonds in the pyrazole ring is that shown in structural Formula 1b:

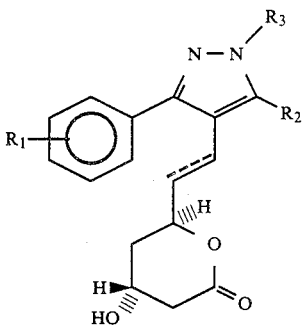

In the structural formula employed throughout this specification and the appended claims, the notation:

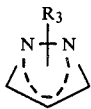

will be employed to denote compounds bearing a single $R_3$ substituent on one nitrogen atom or the other in the pyrazole ring.

In compounds of the present invention, $R_1$ is hydrogen; halogen; straight or branched lower alkyl; hydroxy; straight or branched lower alkyloxy; or straight or branched lower alkanoyl. By the term "lower alkyl" as used throughout this specification and claims is meant straight or branched alkyl of from one to six carbon atoms including, for example, methyl, ethyl, propyl, isopropyl, n-butyl, sec-butyl, isobutyl, tertbutyl, n-pentyl, n-hexyl and the like.

The term "lower alkyloxy" is meant to denote a lower alkyl group as defined above, attached to the parent molecular moiety through an oxygen atom.

The term "lower alkanoyl" is meant to denote a lower alkyl group as defined above, attached through a carbonyl group to the parent molecular moiety.

The term "halogen" denotes fluorine, chlorine, bromine, or iodine.

Halogen substituents are preferred for $R_1$, with fluorine being most preferred.

In accordance with the present invention, $R_2$, may be lower alkyl or trifluoromethyl. Lower alkyl substituents are preferred for $R_2$, with isopropyl (1-methylethyl) being most preferred.

In compounds of the present invention, $R_3$ may be phenyl; benzyl; or phenyl substituted with halogen, hydroxy, nitro, amino, straight or branched alkyl of from one to six carbon atoms, straight or branched alkyloxy of from one to six carbon atoms, methylsulfonyl, methylsulfinyl, acetamido, or benzoyl. Preferred substituents for $R_3$ are phenyl or substituted phenyl, with phenyl being most preferred.

Specific examples of compounds contemplated as falling within the scope of the present invention include the following:

trans-6-[2-[5-(4-fluorophenyl)-3-(1-methylethyl)-1-phenyl-1H-pyrazol-4-yl]ethyl]tetrahydro-4-hydroxy-2H-pyran-2-one;

trans-6-[2-[3-(4-fluorophenyl)-5-(1-methylethyl)-1-phenyl-1H-pyrazol-4-yl]ethyl]tetrahudro-4-hydroxy-2H-p trans-6-[2-[5-(4-fluorophenyl)-3-(1-methyl ethyl)-1-(phenylmethyl)-1H-pyrazol-4-yl]ethyl]tetrahydro-4-hydroxy-2H-pyran-2-one;

trans-6-[2-[3-(4-fluorophenyl)-5-(1-methylethyl)-1-(phenylmethyl)-1H-pyrazol-4-yl]ethyl]tetrahydro-4-hydroxy-2H-pyran-2-one;

trans-6-[2-[5-(4-fluorophenyl)-3-(1-methylethyl)-1-(4-methylphenyl)-1H-pyrazol-4-yl]ethyl]tetrahydro-4-hydroxy-2H-pyran-2-one;

trans-6-[2-[3-(4-fluorophenyl)-5-(1-methylethyl)-1-(4-methylphenyl)-H-pyrazol-4-yl]ethyl]tetrahydro-4-hydroxy-2H-pyran-2-one;

trans-6-[2-[1,5-bis(4-fluorophenyl)-3-(1-methyl-ethyl)-1-(4-methylphenyl)-1H-pyrazol-4-yl]ethyl]tetra-hydro-4-hydroxy-2H-pyran-2-one;

trans-6-[2-[1,3-bis(4-fluorophenyl)-5-(1-methylethyl)-1-(4-methylphenyl)-1H-pyrazol-4-yl]ethyl]tetrahydro-4-hydroxy-2H-pyran-2-one;

R*,R*-5-(4-fluorophenyl)-β,δ-dihydroxy-3-(1methylethyl)-1-phenyl-1H-pyrazole-4-heptanoic acid;

R*,R*-3-(4-fluorophenyl)-β,δ-dihydroxy-5-(1methylethyl)-1-phenyl-1H-pyrazole-4-heptanoic acid;

R*,R*-5-(4-fluorophenyl)-β,δ-dihydroxy-3-(1-methylethyl)-1-(phenylmethyl)-1H-pyrazole-4-heptanoic acid;

R*,R*-3-(4-fluorophenyl)-β,δ-dihydroxy-5-(1-methylethyl)-1-(phenylmethyl)-1H-pyrazole-4-heptanoic acid;

R*,R*-5-(4-fluorophenyl)-β,δ-dihydroxy-3-(1-methylethyl)-1-(4-methylphenyl)-1H-pyrazole-4-heptanoic acid;

R*,R*-3-(4-fluorophenyl)-β,δ-dihydroxy-5-(1-methylethyl)-1-(4-methylphenyl)-1H-pyrazole-4-heptanoic acid;

R*,R*-1,5-bis(4-fluorophenyl)-β,δ-dihydroxy-3-(1-methylethyl)-1H-pyrazole-4-heptanoic acid;

R*,R*-1,3-bis(4-fluorophenyl)-β,δ-dihydroxy-5-(1-methylethyl)-1H-pyrazole-4-heptanoic acid;

R*,R*-7-[5-(4-fluorophenyl)-3-(1-methylethyl)-1-phenyl-1H-pyrazol-4-yl]-3,5-dihydroxy-≠heptenoic acid;

R*,R*-7-[3-(4-fluorophenyl)-5-(1-methylethyl)-1-phenyl-1H-pyrazol-4-yl]-3,5-dihydoxy-heptenoic acid;

The compounds of the present invention are prepared by one of three alternative methods. In the first method, depicted schematically in Reaction Sequence I, and illustrated by Examples 1 and 4-6 below, a substituted pyrazole aldehyde of Formula 8:

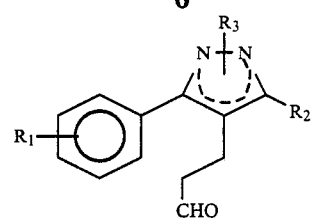
where the dashed lines, $R_1$, $R_2$, and $R_3$ are as previously defined, is first reacted with the
Reaction Sequence I
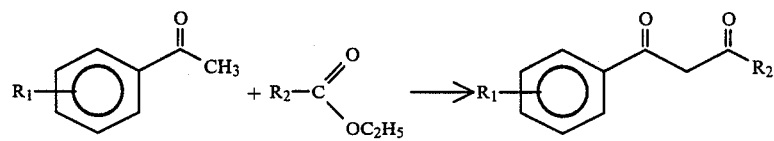
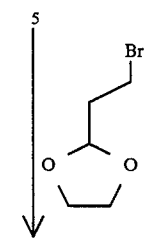
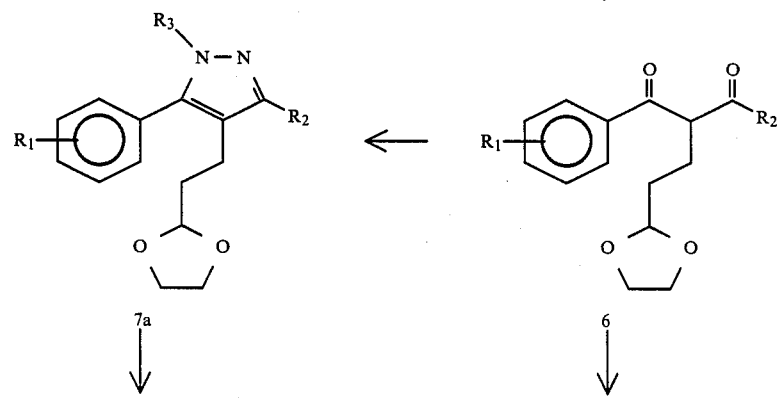

-continued
Reaction Sequence I
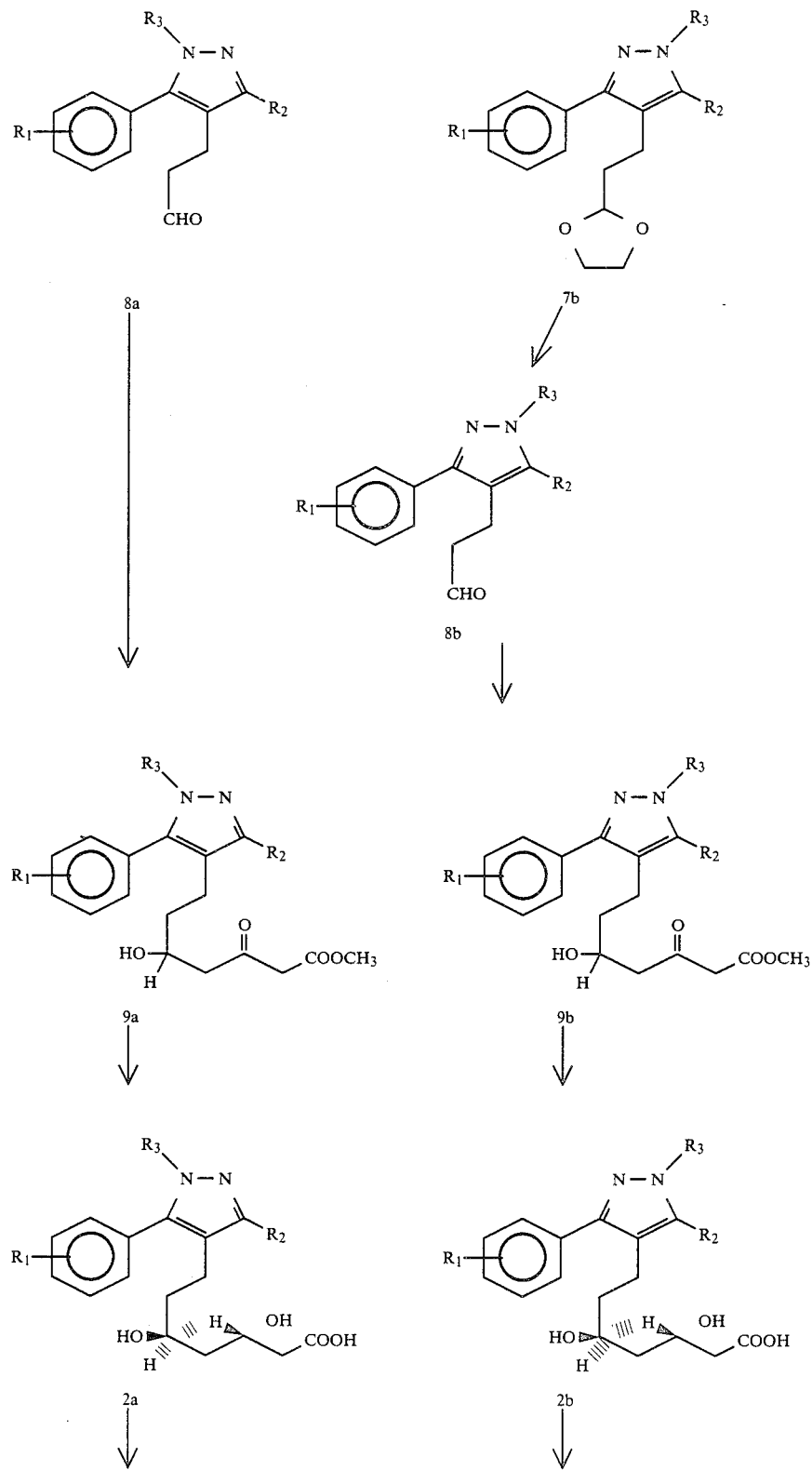

Reaction Sequence I -continued

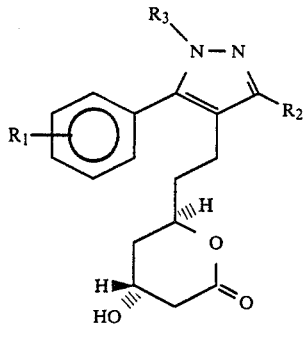
1a

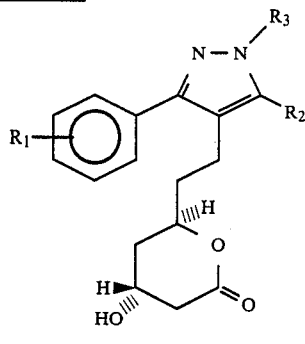
1b dilithio or sodio-lithio salt of methyl acetoacetate (methyl 3-oxo-butanoate) in a polar aprotic organic solvent, such as tetrahydrofuran, to form a hydroxy-keto ester compound for Formula 9:

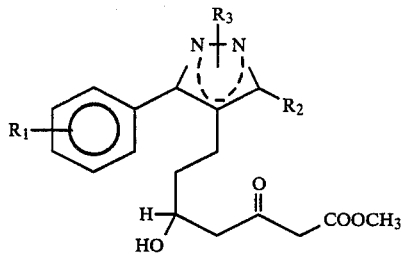
9

The product of this first step is then reduced by a sequence of steps in which it is first dissolved in a polar aprotic organic solvent such as tetrahydrofuran, through which a small amount of air has been bubbled. A slight excess of a trialkylborane such as tributylborane is next added to the mixture which is then cooled to a temperature of preferably between about 0° C. and −78° C., after which sodium borohydride is added.

This mixture is treated with basic aqueous hydrogen peroxide to yield a dihydroxy ester compound of Formula 2':

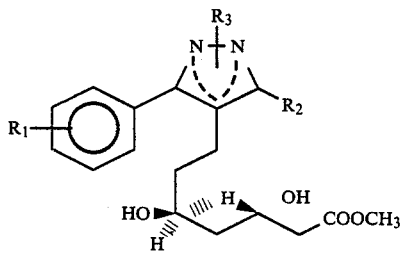
2'

The product mixture contains a predominance of the desired compound in which the two carbon atoms bearing the hydroxy groups are in the desired R*, R* configuration.

The dihydroxy ester compounds of Formula 2' are saponified to the corresponding acids of Formula 2 by the action of aqueous base followed by acidification.

The dihydroxy acids of Formula 2 may be used for the purposes of this invention per se or converted, if desired, to a pharmaceutically acceptable salt by conventional methods. By the term "pharmaceutically acceptable salt" is meant the base addition salts of the carboxylic acid function, formed with pharmaceutically acceptable, nontoxic organic and inorganic bases.

Suitable inorganic bases include the hydroxides, carbonates, bicarbonates, and the like of sodium, potassium, calcium, magnesium, aluminum, iron, and zinc.

Suitable organic bases comprise organic amines which are strong enough bases to form salts with the carboxylic acid function. These pharmaceutically acceptable, nontoxic amines for a class whose limits are readily understood by those skilled in the pharmaceutical formulation arts.

The salts are formed by contacting an aqueous solution or a miscible aqueous-organic solution of the free acid form of the compounds of this invention with an aqueous solution of the desired base, and recovering the salt thus formed by conventional methods such as evaporation or filtration.

The free acid form of the compounds may be recovered from the salts, if desired, by contacting an aqueous solution of the salt with a dilute aqueous solution of an acid such as hydrochloric acid followed by isolation of the free acid in the conventional manner such as by extraction or filtration.

Alternatively, the dihydroxy acids of Formula 2 are converted, if desired, to the lactone form (Formula 1) by heating in a high-boiling inert hydrocarbon solvent such as benzene, toluene, or xylene or the like with azeotropic removal of water.

Intermediate compounds of structure 8 are produced by the general synthetic methods presented in Reaction Sequence I. The known substituted acetophenone compounds, 3, where $R_1$ is as previously defined, are reacted with a strong base such as sodium hydride in a polar aprotic organic solvent such as tetrahydrofuran or dioxane, and then with a compound of Formula 4, where $R_2$ is lower alkyl or trifluoromethyl, to produce the diketone compounds of Formula 5. (For a description of this condensation reaction, see J. Am. Chem. Soc., 66: 1220–1222 (1944)).

The diketone compounds of Formula 5 are next alkylated with 2-(2-bromoethyl)-1,3-dioxolane in the presence of sodium iodide to produce the compounds of Formula 6 by first reacting the diketone, 5, with a strong base such as sodium hydride in a polar aprotic organic solvent such as tetrahydrofuran or dimethyl formamide.

The alkylated diketone compounds, 6, are next converted to the substituted pyrazoles, 7a and 7b, by reaction with the desired substituted hydrazine. Addition of the substituted hydrazine to the diketone compound, 6, can occur in either of two ways, leading independently to compound 7a or compound 7b. The product of the reaction is a mixture of the two condensation compounds, with the $R_3$ substituent being attached to one nitrogen atom or the other of the resulting pyrazole ring. The product mixture is separated by conventional means such as chromatography to obtain the individual isomers.

The ratio of the two products, 7a and 7b, can be varied by a choice of the conditions under which the condensation reaction is carried out. For example, in absolute ethanol under reflux, a mixture of the two isomeric products is obtained, with 7a being obtained in higher yield than 7b. In acetic acid, the product is almost exclusively 7a.

The substituted pyrazole compounds 7a or 7b are finally deprotected by reaction with, for example, 70% aqueous acetic acid to produce the substituted pyrazole aldehyde compounds 8a or 8b.

The second method of making compounds of the present invention is depicted schematically in Reaction Sequence II and is illustrated by Example 2 below.

Propenal, 10, is reacted with the dilithio or sodiolithio salt of methyl acetoacetate (methyl 3-oxo-butanoate) in a polar aprotic organic solvent such as tetrahydrofuran or dioxane, to form 5-hydroxy-3-oxo-6-heptanoic acid, methyl ester, 11. The product of this reaction is then reduced by a sequence of steps in which it is first dissolved in a polar aprotic organic solvent such as tetrahydrofuran, through which a small amount of air has been bubbled. A slight excess of a trialkylborane, such as tributylborane, is next added to the mixture which is then cooled to a temperature of preferably between 0° C. and −78° C., after which sodium borohydride is added. The mixture is next treated with a basic aqueous solution of hydrogen peroxide to produce 3,5-dihydroxy-6-heptanoic acid, methyl ester, 12, in which the R*,R* isomer predominates.

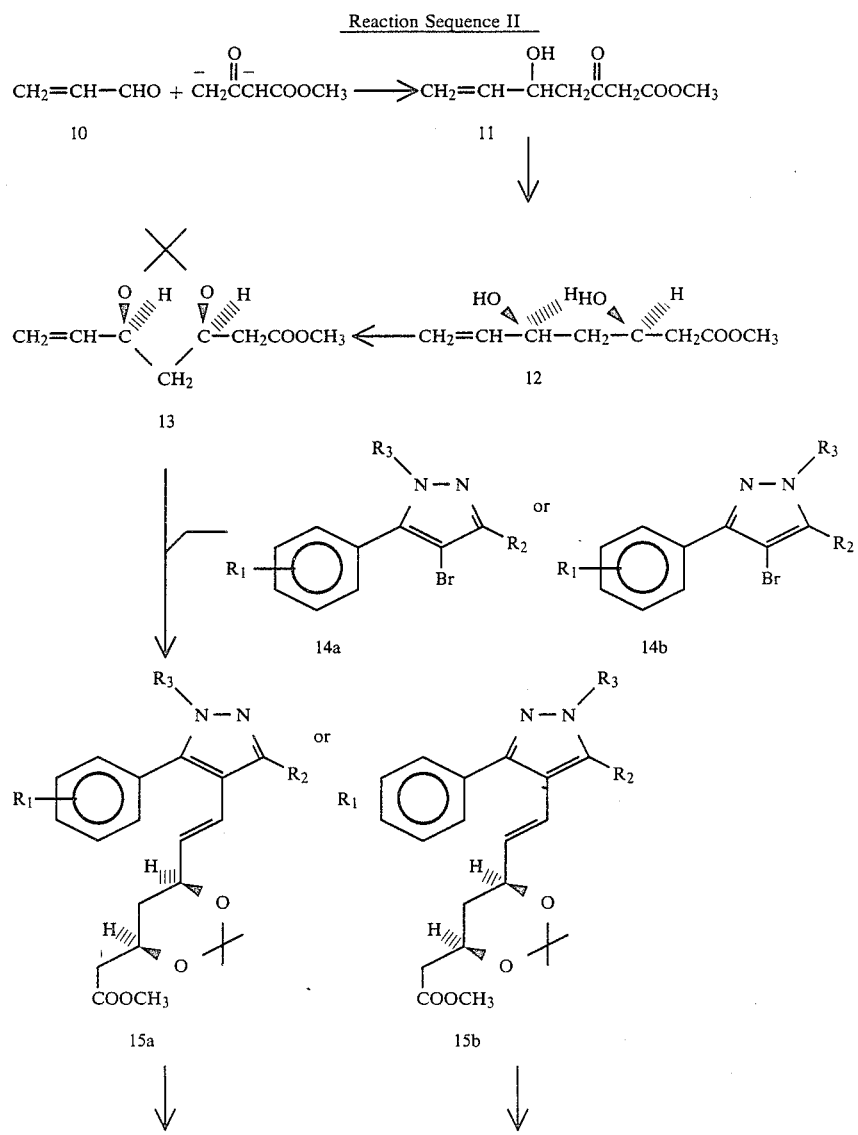

Reaction Sequence II -continued

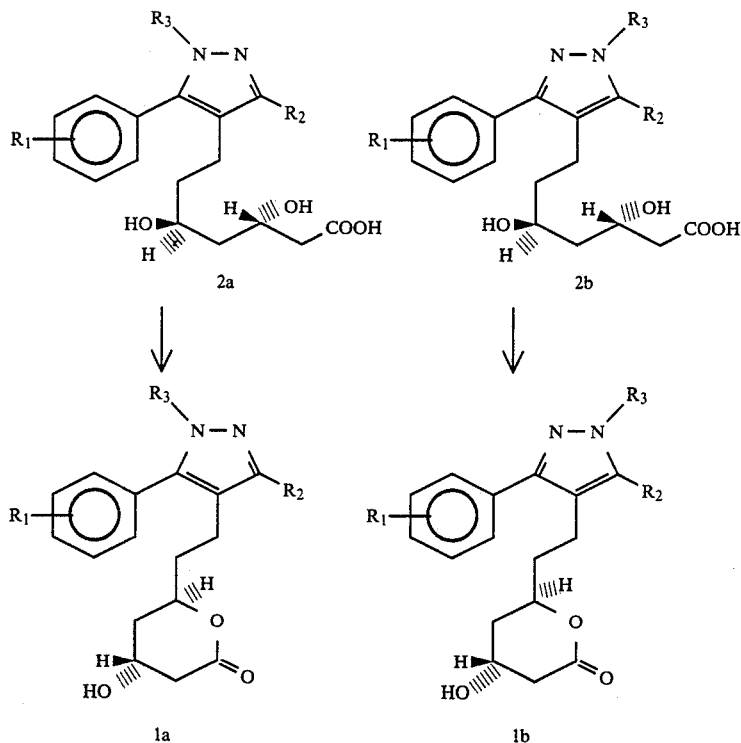

The two hydroxyl groups of compound 12 are next protected by reaction of 12 with dimethoxypropane in the presence of a small amount of camphorsulfonic acid to produce compound 13.

Compound 13 is reacted with a substituted 4-bromopyrazole compound of Formula 14a or 14b to produce the coupled product 15a or 15b. This coupling reaction is carried out in the presence of bis(triphenylphosphine)palladium chloride catalyst in a suitable solvent such as a 50:50 mixture of triethylamine and dimethylformamide.

The substituted 4-bromopyrazole compounds, 14a and 14b, are prepared from the parent substituted pyrazole compounds by reaction with N-bromosuccinimide in the conventional manner. The substituted 4-iodopyrazole compounds may also be employed for the coupling reaction, the iodo compounds being prepared from the parent substituted pyrazoles by reaction with N-iodosuccinimide.

The double bond in the alkenyl bridge of compound 15a or 15b is catalytically reduced by hydrogen at ambient pressure in the presence of a suitable catalyst such as palladium on carbon, and the hydroxy groups are deprotected and the ester hydrolyzed by aqueous acid in the conventional manner to produce the acids 2a and 2b. The acids are lactonized to the compounds of Formula 1a and 1b, if desired, by heating in a high boiling inert hydrocarbon such as benzene, toluene, or xylene with azeotropic removal of water.

The third method of making compounds of the present invention is particularly adapted for making compounds where the substituted pyrazole ring and the hydroxy-lactone ring are bridged by an unsaturated two-carbon chain. This method is depicted schematically in Reaction Sequence III and illustrated by Example 3 below.

According to this method, the substituted 4-bromo- or 4-iodopyrazole compounds (see Reaction Sequence II, compounds 14a or 14b) are coupled with methyl or ethyl acrylate in the presence of bis(triphenylphosphine)palladium chloride to produce compound 16a or 16b.

These esters are reduced by the action of a metal hydride such as, for example, diisobutyl aluminum hydride to the corresponding alcohols 17a and 17b. The hydroxyl function of compounds 17a and 17b are oxidized to the corresponding aldehyde compounds 18a and 18b by means of a mild oxidizing agent such as manganese dioxide.

In subsequent reaction steps, corresponding to those detailed in Reaction Sequence I, (1) the aldehydes are coupled with the dianion of methyl acetoacetate to produce the corresponding 3-oxo-5-hydroxy-6-heptenoic acid esters; (2) the ketone function is reduced; (3) the ester is saponified to produce the acid; and (4) the acid is lactonized, if desired to produce the compounds of Formula 1.

In this reaction sequence, the lactonization step is most efficiently carried out by the aid of a coupling reagent such as dicyclohexylcarbodiimide in cold dichloromethane.

The antimicrobial susceptibilities of eleven strains of *Candida albicans*, two strains of *Candida tropicans*, and one strain each of *Toru-lopsis glabrata* and *Cryptococcus neoformans* to representative compounds of the present invention were tested. For comparison, the known antifungal agents amphotericin-B and ketoconazole were also tested. Minimal inhibitory concentrations (MIC's) for each compound were determined Reaction Sequence III

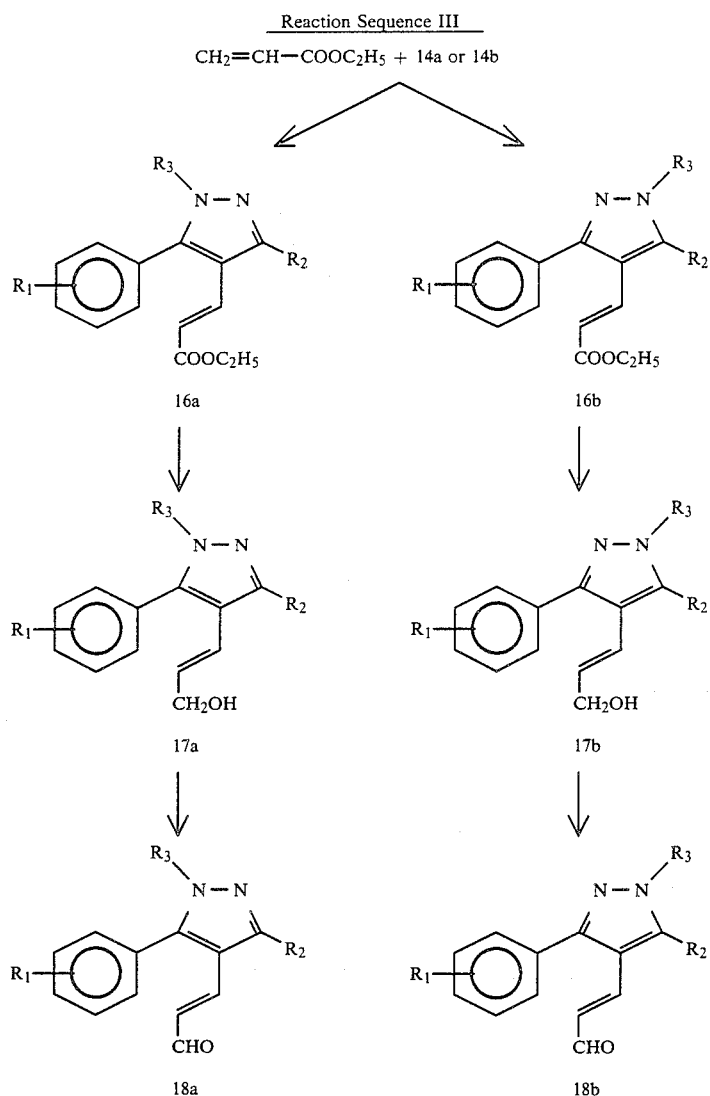

using the microbroth dilution technique described by S. Shadomy et al, "Laboratory Studies with Antifungal Agents: Susceptibility Tests and Bioassays," pp. 991-999 in *Manual Clin. Microbiol.*, 4th Ed., Amer. Soc. for Microbiol., Washington, D.C., 1985. The compounds tested are as follows and the results of the testing appear in the following Table.

Compound 1—trans-(±)-6-[2-[5-(4-Fluorophenyl)-3-(1-methylethyl)-1-phenyl-1H-pyrazol-4-yl]ethyl]tetrahydro-4-hydroxy-2H-Pyran-2-one.

Compound 2—5-(4-fluorophenyl)-$\beta,\delta$-dihydroxy-3-(1-methylethyl)-1-phenyl-1H-Pyrazole-4-heptanoic acid, monosodium salt.

In therapeutic use as antifungal agents, the compounds are administered to the patient, preferably by oral administration, at dosage levels of from 40 mg to 600 mg per day. For a normal human adult of approximately 70 kg body weight, this translates into a dosage of about 0.5 mg/kg to about 8.0 mg/kg of body weight per day. The dosages may, however, be varied depending upon the condition and prior medical history of the patient, the severity of the condition being treated, and the activity of the compound employed in the pharmaceutical composition. Determination of the optimal dose in a particular case is within the skill of the art.

The daily dose may be administered once daily to the subject, or may be divided and administered in several separate doses in a single twenty-four hour period, for convenience.

TABLE

| Microorganism (Strain) | Antifungal Activity MIC ($\mu$g/ml) at 24 Hours for Compound | | | |
|---|---|---|---|---|
| | AMP-B* | Keto** | 1 | 2 |
| *Candida albicans* | | | | |
| B4b | 4 | .25 | 64 | 64 |
| M752 | 8 | .25 | 128 | 128 |
| ATCC 10231 | 4 | >.5 | 64 | 64 |
| 1570 | 8 | .25 | 64 | 64 |
| 1571 | 2 | .125 | 64 | 64 |
| 1574 | 4 | .25 | 64 | 64 |
| 1575 | 8 | .5 | 64 | 64 |
| 1576 | 4 | >.5 | 64 | 64 |
| 1577 | 8 | .125 | 32 | 64 |
| 1578 | 8 | .25 | 64 | 64 |
| 1579 | 4 | .5 | 64 | 64 |
| *Candida tropicans* | | | | |
| ATCC 13803 | 8 | .5 | >128 | >128 |
| 1573 | 4 | >.5 | 64 | 64 |

TABLE-continued

Antifungal Activity

| Microorganism (Strain) | MIC (μg/ml) at 24 Hours for Compound | | | |
|---|---|---|---|---|
| | AMP-B* | Keto** | 1 | 2 |
| *Torulopsis glabrata* 1581 | 8 | >.5 | 128 | >128 |
| *Cryptococcus neoformans* 1678 | 4 | >.5 | 128 | 128 |

*Amphotericin-B
**Ketoconazole

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents. It can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppository preparations, a low-melting wax such as a mixture of fatty-acid glycerides and cocoa butter is melted, and the active ingredient is dispersed homogeneously therein, as by stirring. The moltent homogeneous mixture is then poured into conveniently sized molds and allowed to cool and solidify.

Powders and tablets preferably contain about 5% to about 70% of the active ingredient. Examples of suitable solid carriers are magnesium stearate, magnesium carbonate, talc, sugar, lactose, pectin, dextrin, starch, tragacanth, methyl cellulose, sodium carboxymethyl cellulose, and the like.

The term "preparation" is intended to include the formulation of the active compound with encapsulating material as carrier providing a capsule in which the active component (with or without other carriers) is surrounded by carrier. Similarly, cachets are included. Tablets, powders, cachets, and capsules can be used as solid dosage forms suitable for oral administration.

Liquid form preparations include solutions, emulsions, and suspensions. Liquid preparations can be formulated in aqueous solution or in aqueous/alcohol solution with such materials as polyethylene glycol. Such solutions are prepared by dissolving the active component in water or aqueous/alcohol solution and adding suitable colorants, flavoring agents, stabilizers, and thickening agents as desired. Aqueous suspensions for oral use can be made by dispersing the finely divided active compound in water with viscous material, i.e. natural or synthetic gums, resins, methyl cellulose, sodium carboxymethyl cellulose, and other well-known suspending agents.

Preferably, the pharmaceutical preparation is in unit dosage form. In such form, the preparation is subdivided into using doses containing appropriate quantities of the active component. The unit dosage form can be a packaged preparation, the package containing discrete quantities of preparation, for example packeted tablets, capsules, or powders in vials or ampoules. The unit dosage form can also be a capsule, cachet, or tablet itself or can be the appropriate number of any of these packaged forms.

EXAMPLE 1

Preparation of trans-6-[2-[5-(4-fluorophenyl)-3-(1-methylethyl)-1-phenyl-1H-pyrazol-4-yl]-ethyl]tetrahydro-4-hydroxy-2H-pyran-2-one - Method 1

Step A—Preparation of 1-(4-fluorophenyl)-4-methyl-1,3-pentanedione

A mixture of 4-fluoroacetophenone (150 g, 1.09 mol) and ethyl isobutyrate (126 g, 1.09 mol) in 1.5 liters of dioxane was added dropwise under a nitrogen atmosphere to a vigorously stirred suspension of hexane-washed sodium hydride (133 g, 3.25 mol, 58.8% NaH) in 3.0 liters of dioxane. Vigorous evolution of gas ensued, after which the mixture was heated to 80°-90° C. for four hours.

The mixture was then allowed to cool to room temperature after which it was poured into 6 liters of 2M hydrochloric acid. The resulting mixture was cooled to 0° C. with vigorous stirring and extracted four times with 1-liter portions of chloroform.

The combined chloroform extracts were washed twice with 500-ml portions of water, twice with 500-ml portions of brine solution, and then dried over anhydrous magnesium sulfate. The mixture was filtered to remove undissolved solids, and the filtrate was concentrated under vacuum.

Distillation of the residue yielded 116 g (50%) of 1-(4-fluorophenyl)-4-methyl-1,3-pentanedione, b.p. 100°-110° C. at 1 Torr. The infrared spectrum of a thin film of the product showed principal absorption peaks at 2973 and 1603 cm$^{-1}$.

The 100 MHz proton magnetic resonance spectrum of the product in deuterochloroform showed peaks at 1.25 (doublet, J=7 Hz, 6 protons), 2.60 (multiplet, J=7 Hz, 1 proton), 6.1 (multiplet, 2 protons), 6.1 (singlet, 1 proton), 7.15 (multiplet, 2 protons), and 7.9 (multiplet, 2 protons) parts per million downfield from the tetramethylsilane signal.

Step B—Preparation of 2-[2-(1,3-dioxolan-2-yl)ethyl]-1-(4-fluorophenyl)-4-methyl-1,3-pentanedione To a suspension of 22.8 g (0.56 mol, 58.8% NaH) of hexane-washed sodium hydride in 750 ml of anhydrous dimethylformamide was added dropwise, with stirring, a mixture of 450 ml of anhydrous dimethylformamide and 116 g (0.56 mol) of 1-(4-fluorophenyl)-4-methyl-1,3-pentanedione, prepared in Step A above. Vigorous effervescence ensued.

When gas evolution had ceased, 21 g (0.14 mol) of sodium iodide were added, followed by the dropwise addition of 100.9 g (0.56 mol) of 2-(2-bromoethyl)-1,3-dioxolane in 450 ml of anhydrous dimethylformamide.

The resulting mixture was heated at 80°-90° C. for 36 hours after which time it was cooled to room temperature and poured into 2 liters of ice-water. The emulsion which formed was extracted four times with 1-liter portions of chloroform. The combined chloroform extracts were washed successively with 500-ml portions of water and brine and then dried over anhydrous magnesium sulfate. The dried chloroform extracts were filtered, and the filtrate was concentrated under vacuum. The residue was flash-chromatographed on silica gel, eluting with 25% ethyl acetate-hexane to yield 100 g (58%) of 2-[2-(1,3-dioxolan-2-yl)-ethyl]-1-(4-fluorophenyl)-4-methyl-1,3-pentane-dione.

The infrared spectrum of a thin film of the product showed principal absorption peaks at 2972, 1723, 1676, 1600, and 1237 cm$^{-1}$.

The 100 MHz proton magnetic resonance spectrum of a deuterochloroform solution of the product showed peaks at 1.1 (doublet, 6 protons), 1.7 (multiplet, 2 protons), 2.2 (multiplet, 2 protons), 2.8 (multiplet, 1 proton), 3.9 (multiplet, 4 protons), 4.7 ( triplet, 1 proton), 4.9 (triplet, 1 proton), 7.2 (multiplet, 2 protons), and 8.1 (multiplet, 2 protons) parts per million downfield from the tetramethylsilane signal.

Step C—Preparation of 4-[2-(1,3-dioxolan-2-yl)ethyl]-5-(4-fluorophenyl)-3-(1-methylethyl)-1-phenyl-1H-pyrazole To a solution of 104.75 g (0.34 mol) of 2-[2-(1,3-dioxolan-2-yl)ethyl]-1-(4-fluorophenyl)-4-methyl-1,3-pentanedione in 1 liter of absolute ethanol were added dropwise, under nitrogen with stirring, 40.45 g (0.374 mol) of phenylhydrazine.

When addition was complete, the mixture was heated under reflux for five days, and then cooled to room temperature. After concentrating the mixture, the residue was chromatographed on silica gel, eluting with 15% ethyl acetate-hexane to yield 50.85 g (40%) of 4-[2-(1,3-dioxolan-2-yl)-ethyl]-5-(4-fluorophenyl)-3-(1-methylethyl)-1- phenyl-1H-pyrazole.

The infrared spectrum (KBr pellet) of the product showed principal absorption peaks at 2950, 1596, 1511, 1377, and 1143 cm$^{-1}$.

The 100 MHz proton magnetic resonance spectrum of a deuterochloroform solution of the product showed peaks at 1.25 (doublet, 6 protons), 1.8 (multiplet, 2 protons), 2.7 (multiplet, 2 protons), 3.1 (triplet, 1 proton), 3.9 (multiplet, 4 protons), 4.8 (triplet, 1 proton) and 7.2 (multiplet, 9 protons) parts per million downfield from the tetramethylsilane signal.

Step D—Preparation of 5-(4-fluorophenyl)-3-(1-methylethyl)-1-phenyl-1H-pyrazol-4-propanal A solution of 50.85 g (0.134 mol) of 4-[2-(1,3-dioxolan-2-yl)ethyl]-5-(4-fluorophenyl)-3-(1-methylethyl)-1-phenyl-1H-pyrazole in 1 liter of 70% aqueous acetic acid was heated under reflux for two days. At the end of this time, the solution was cooled to room temperature and partitioned between 1 liter or water and 1 liter of chloroform.

The phases were separated and the aqueous phase was extracted with a further 1-liter portion of chloroform. The chloroform solutions were combined and washed successively with 250-ml portions of saturated aqueous sodium bicarbonate solution, water, and brine.

The chloroform solution was then dried over anhydrous magnesium sulfate, filtered, and concentrated under vacuum. The residue was flash-chromatographed on silica gel, eluting with 15% ethyl acetate-hexane. The eluted material solidified, and was recrystallized from hexane to yield 29 g (65%) of 5-(4-fluorophenyl)-3-(1-methylethyl)-1-phenyl-1H-pyrazol-4-propanal, m.p. 86°–88° C.

The infrared spectrum of the product (KBr pellet) showed principal absorption peaks at 2961 and 1728 cm$^{-1}$.

The 100 MHz proton magnetic resonance spectrum of a deuterochloroform solution of the product showed peaks at 1.36 (doublet, 6 protons), 2.4 (triplet, 2 protons), 2.7 (triplet, 2 protons), 3.05 (multiplet, 1 proton), 7.2 (multiplet, 9 protons), and 9.6 (singlet, 1 proton) parts per million downfield from the tetramethylsilane signal.

Step E—Preparation of 5-(4-fluorophenyl)-δ-hydroxy-3-(1-methylethyl)-β-oxo-1-phenyl-1H-pyrazole-4-heptanoic acid, methyl ester To a stirred suspension of 4.56 g (0.116 mol, 58.8% NaH) of hexane-washed sodium hydride in 100 ml of anhydrous tetrahydrofuran which had been cooled to 0° C. under nitrogen, was added over a period of sixty minutes, a solution of 11.48 ml (0.106 mol) of methyl acetoacetate in 100 ml of anhydrous tetrahydrofuran. When gas evolution was complete, 40.88 ml of a 2.6 molar hexane solution of n-butyl lithium was added dropwise over a period of thirty minutes. The resulting solution was stirred for an additional sixty minutes at 0° C. and then cooled to −78° C. A solution of 23.86 g (0.0709 mol) of 5-(4-fluorophenyl)-3-(1-methylethyl)--1-phenyl-1H-pyrazol-4-propanal in 100 ml of anhydrous tetrahydrofuran was then added dropwise over a period of eighty minutes.

The resulting solution was stirred for thirty minutes at −78° C. and then at 0° C. for thirty minutes after which the reaction was quenched by the addition of 35 ml of glacial acetic acid. The cooling bath was removed from around the reaction flask, and 70 ml of 2 M hydrochloric acid were added. The resulting mixture was vigorously stirred, and then partitioned between 750 ml of diethyl ether and 250 ml of water.

The aqueous layer was extracted with 200 ml of diethyl ether, and the combined ether extracts were washed with successive 200-ml portions of 0.2 M hydrochloric acid and water, followed by three successive washings with 150-ml portions of saturated sodium bicarbonate solution and once with a 200-ml portion of brine. The ether solution was dried over anhydrous magnesium sulfate and then flash-chromatographed on silica gel, eluting with 40% ethyl acetatehexane. This procedure yielded 32.3 g (83.5%) of 5-(4-fluorophenyl)-δ-hydroxy-3-(1-methylethyl)-β-oxo-1-phenyl-1H-pyrazole-4-heptanoic acid, methyl ester.

Step F—Preparation of R*,R*-5-(4-fluorophenyl)-β,δ,-dihydroxy-3-(1-methylethyl)-1-phenyl-1H-pyrazole-4-heptanoic acid and trans-6-[2-[5-(4-fluorophenyl)-3-(1-methylethyl)-1-phenyl-1H-pyrazol-4-yl]-ethyl]tetrahydro-4-hydroxy-2H-pyran-2-one By means of a syringe 125 ml of air were bubbled through a solution of 0.076 mol of tributylborane and 31.48 g (0.070 mol) of 5-(4-fluorophenyl)-δ-hydroxy-3-(1-methylethyl)-β-oxo-1-phenyl-1H-pyrazole-4-heptanoic acid, methyl ester in 150 ml of anhydrous tetrahydrofuran at room temperature under nitrogen.

The resulting solution was stirred at room temperature overnight, and then cooled to −78° C. To the cooled mixture were added 3.154 g (0.0835 mol) of sodium borohydride. The mixture was allowed to warm to −20° C. over a period of two hours, and then to 0° C. where it was stirred for sixty minutes.

The reaction was then quenched by the addition of 14.6 ml (0.205 mol) of glacial acetic acid and 17 ml of water. When gas evolution had ceased, 167 ml of 3 M sodium hydroxide were added, followed by the dropwise addition of 25.7 ml of 30% hydrogen peroxide (0.2505 mol) over a period of sixty minutes.

The resulting mixture was allowed to warm to room temperature overnight, and was partitioned between 500 ml of diethyl ether and 500 ml of water. The ether layer was separated, washed with 400 ml of 2 M hydrochloric acid, and then extracted twice with 500-ml portions of ethyl acetate.

The extract was dried over anhydrous magnesium sulfate, filtered, and evaporated to yield 30 g of R*,R*-5-(4-fluorophenyl)-β,δ-dihydroxy-3-(1-methylethyl)-1-phenyl-1H-pyrazole-4-heptanoic acid as an oil.

This material was dissolved in 500 ml of toluene and heated under reflux (with azeotropic removal of water) for three hours. The mixture was cooled to room temperature, and the solvent removed under vacuum. The oil which remained was flash-chromatographed on silica gel, eluting with 75% ethyl acetate-hexane to provide 16.6 g of a colorless solid. Recrystallization from 5:1 cyclohexane-chloroform provided 13.6 g of trans-6-[2-[5-(4-fluorophenyl)-3-(1-methylethyl)-1-phenyl-1H-pyrazol-4-yl]ethyl]tetrahydro-4-hydroxy-2H-pyran-2-one, m.p. 157–159° C.

Analyzed for $C_{25}H_{27}FN_2O_3$: Calc. : C, 71.06%; H, 6.44%; N, 6.63%; Found : C, 70.80%; H, 6.62%; N, 6.66%;

The infrared spectrum of the product (KBr pellet) showed principal absorption peaks at 3400, 1707, 1511, 1252, 1224, and 1024 $cm^{-1}$.

The 100 MHz proton magnetic resonance spectrum of a deuterochloroform solution of the product showed peaks at 1.3 (doublet, 6 protons), 1.6-1.9 (multiplet, 4 protons), 2.1 (broad singlet, 1 proton), 2.6 (multiplet, 4 protons), 3.0 (multiplet, 1 proton), 4.3 (multiplet, 1 proton), 4.6 (multiplet, 1 proton), and 7.2 ((multiplet, 9 protons) parts per million downfield from the tetramethylsilane signal.

EXAMPLE 2

Preparation of trans-6-[2-[5-(4-fluorophenyl)-3-(1-methylethyl)-1-phenyl-1H-pyrazol-4-yl]ethyl]tetrahydro-4-hydroxy-2H-pyran-2-one - Method 2

Step A—Preparation of 1-(4-fluorophenyl)-4methyl-1,3-pentanedione

Employing the procedure of Step A of Example 1, 12.0 g of 1-(4-fluorophenyl)-4-methyl-1,3-pentanedione were prepared.

Step B—Preparation of 5-(4-fluorophenyl)-3-(1-methylethyl)-1-phenyl-1H-pyrazole To a solution of 50.9 mmol of 1-(4-fluorophenyl)-4-methyl-1,3-pentanedione in glacial acetic acid were added, at room temperature, 55.9 mmol of phenylhydrazine. The mixture was stirred overnight at room temperature, and then partitioned between 200 ml of diethyl ether and 50 ml of water. The organic layer was separated, washed successively with saturated sodium bicarbonate solution, brine, and then dried over anhydrous magnesium sulfate.

The crude product was flash-chromatographed on silica gel, eluting first with 100% hexane, then 10% ethyl acetate-hexane, and finally with 20% ethyl acetate-hexane, to yield 12.0 g (84%) of solid 5-(4-fluorophenyl)-3-(1-methylethyl)-1-phenyl-1H-pyrazole.

The 100 MHz proton magnetic resonance spectrum of a deuterochloroform solution of the material showed peaks at 1.30 (doublet, J=7 Hz, 6 protons), 3.05 (septet, J=7 Hz, 1 proton), 6.22 (singlet, 1 proton), and 6.7-7.5 (multiplet, 9 protons) parts per million downfield from the tetramethylsilane signal.

Step C—Preparation of 4-bromo-(5-fluorophenyl)-3-(1-methylethyl)-1-phenyl-1H-pyrazole N-Bromosuccinimide (40.3 mmol) was added to a mixture of 40.3 mmol of 5-(4-fluorophenyl)-3-(1-methylethyl)-1-phenyl-1H-pyrazole and 60 ml of dimethylformamide at 0° C. The resulting mixture was stirred at 0° C. for one-half hour, after which time it was partitioned between 250 ml of diethyl ether and 100 ml of water.

The water layer was extracted with ether and the combined ether extracts were diluted with hexane and washed once with saturated sodium bicarbonate solution, twice with brine solution, and then dried over anhydrous magnesium sulfate. The ether was evaporated and the solid residue recrystallized from ether/hexane to yield 9.72 g (67%) of 4-bromo-(5-fluorophenyl)-3-(1-methylethyl)-1-phenyl-1H-pyrazole.

The 100 MHz proton magnetic resonance spectrum of a deuterochloroform solution of the product showed peaks at 1.35 (doublet, J=7 Hz, 6 protons), 3.13 (septet, J=7 Hz, 1 proton), and 6.8-7.3 (multiplet, 9 protons), parts per million downfield from the tetramethylsilane signal.

Step D—Preparation of 5-hydroxy-3-oxo-6-heptenoic acid, methyl ester

Propenal (0.1 mol, as a 2 M solution in tetrahydrofuran) was added dropwise over a period of thirty minutes to a stirred solution of 0.11 mol of the dianion of methyl acetoacetate (prepared by the method of Step E of Example 1) in 200 ml of tetrahydrofuran which had been cooled to 0° C. When addition was complete, the solution was stirred for thirty minutes after which the reaction was quenched by the addition of saturated ammonium chloride solution, followed by 2 M hydrochloric acid solution.

The reaction mixture was extracted with diethyl ether and the ether extract was washed successively with water, saturated sodium bicarbonate solution, and then brine. The ether solution was then dried over anhydrous magnesium sulfate, filtered, and evaporated to yield 14 g of 5-hydroxy-3-oxo-6-heptenoic acid, methyl ester, contaminated with a slight amount of methyl acetoacetate starting material.

Step E—Preparation of β,δ-dihydroxy-6-heptenoic acid, methyl ester

Employing a syringe, 10 ml of air were bubbled through a solution of 10 mmol of 5-hydroxy-3-oxo-6-heptenoic acid, methyl ester and 11 mmol of tributylborane dissolved in 10 ml of anhydrous tetrahydrofuran which was under a nitrogen atmosphere. The resulting mixture was stirred overnight, then cooled to −78° C. after which 12 mmol of sodium borohydride were added. The suspension was allowed to warm slowly to 0° C., at which point the reaction was quenched by the addition of 30 mmol of glacial acetic acid. Methanol (30 ml) was added, followed by 3.3 ml of 30% aqueous hydrogen peroxide solution. This mixture was stirred at 0° C. for sixty minutes, and then partitioned between diethyl ether and water.

The organic layer was separated, washed with brine solution, and then dried over anhydrous magnesium sulfate. The ether solution was evaporated to yield crude β,δ-dihydroxy-6-heptenoic acid, methyl ester which was used in the subsequent step without further purification.

Step F—Preparation of 6-ethenyl-2,2-dimethyl-1,3-dioxane-4-acetic acid, methyl ester The crude β,δ-dihydroxy-6-heptenoic acid, methyl ester from the previous step was dissolved in a mixture of 30 ml of dichloromethane and 10 ml of 2,2-dimethoxypropane. Camphorsulfonic acid (0.05 g) was added, and the mixture was stirred overnight. Concentration of the reaction mixture and flashchromatography of the residue yielded 1.1 g of 6-ethenyl-2,2-dimethyl-1,3-dioxane-4- acetic acid, methyl ester which was employed in the subsequent step without further purification.

The infrared spectrum of a liquid film of the product showed principal absorption peaks at 2994, 1743, 1439, 1382, 1203, and 1170 cm$^{-1}$.

The 90 MHz proton magnetic resonance spectrum of a deuterochloroform solution of the product showed peaks at 1.2–1.3 (multiplet, 1 proton), 1.38 (singlet, 3 protons), 1.45 (singlet, 3 protons), 1.60 (multiplet, 1 proton), 3.62 (singlet, 3 protons), 4.1–4.4 (multiplet, 2 protons), and 5.0–6.0 (multiplet, 3 protons) parts per million downfield from the tetramethylsilane signal.

Step G—Preparation of 6-[2-[5-(4-fluorophenyl)-3-(1-methylethyl)-1-phenyl-1H-pyrazol-4-yl]-ethenyl]-2,2-dimethyl-1,3-dioxane-4-acetic acid, methyl ester bis(Triphenylphosphine) palladium chloride (2 mol%) was added to a stirred solution of 6-ethenyl-2,2-dimethyl-1,3-dioxane-4-acetic acid, methyl ester (5.13 mmol) and 4-bromo-5-(4-fluorophenyl)-3-(1-methylethyl)-1-phenyl-1H-pyrazole (3 mmol, prepared as described above in Step C of this Example) in 6 ml of a 50:50 mixture of triethylamine and dimethylformamide.

The resulting solution was heated to 115° C. for two hours after which time a further 1.5 mol% of catalyst was added. The mixture was stirred at 115° C. for an additional eighteen hours and then cooled to room temperature. The cooled solution was diluted with diethyl ether, washed successively with dilute hydrochloric acid, saturated sodium bicarbonate, and brine. The organic solution was dried over anhydrous magnesium sulfate, filtered and concentrated. The residue was flash-chromatographed on silica gel to yield 0.74 g (50%) of 6-[2-[5-(4-fluorophenyl)-3-(1-methylethyl)-1-phenyl-1H-pyrazol-4-yl]ethenyl]-2,2-dimethyl-1,3-dioxane-4-acetic acid, methyl ester which was employed in the subsequent step without further purification.

The 200 MHz proton magnetic resonance spectrum of a deuterochloroform solution of the product showed peaks at 1.3–1.7 (multiplet, 14 protons), 2.36 (doublet of doublets, J=14, 6 Hz, 1 proton), 2.56 (doublet of doublets, J=14, 6 Hz, 1 proton), 3.20 (septet, J=7 Hz, 1 proton), 3.67 (singlet, 3 protons), 4.30 (multiplet, 2 protons), 5.65 (doublet of doublets, J=15, 7 Hz, 1 proton), 6.33 (doublet, J=15 Hz, 1 proton), and 7.0–7.3 (multiplet, 9 protons) parts per million downfield from the tetramethylsilane signal.

Step H—Preparation of R*,R*-5-(4-fluorophenyl)-β,δ-dihydroxy-3-(1-methylethyl)-1-phenyl-1H-pyrazole-4-heptanoic acid A solution of 6-[2-[5-(4-fluorophenyl)-3-(1-methylethyl)-1-phenyl-1H-pyrazol-4-yl]ethenyl]-2,2-dimethyl-1,3-dioxane-4-acetic acid, methyl ester (0.63 g, 1.28 mmol) in 10 ml of ethyl acetate was hydrogenated at one atmosphere of hydrogen, employing 10% Pd/C as a catalyst at 25° C. for two days. The catalyst was filtered off, and the filtrate concentrated. The residue was dissolved in 30 ml of 50:50 tetrahydrofuran/1 M hydrochloric acid and stirred for five hours.

Sodium hydroxide solution was added until the mixture was basic, and the mixture was stirred for thirty minutes. The resulting mixture was diluted with water, extracted with diethyl ether, and then acidified. The acidified mixture was extracted twice with ethyl acetate, and the combined extracts were washed with brine and dried over anhydrous magnesium sulfate to yield R*,R*-5-(4-fluorophenyl)-β,δ-dihydroxy-3-(1-methylethyl)-1-phenyl-1H-pyrazole-4-heptanoic acid.

Step I—Preparation of trans-6-[2-[5-(4-fluorophenyl)-3-(1-methylethyl)-1-phenyl-1H-pyrazol-4-yl]tetrahydro-4-hydroxy-2H-pyran-2-one The R*,R*-5-(4-fluorophenyl)-β,δ-dihydroxy-3-(1-methylethyl)-1-phenyl-1H-pyrazole-4-heptanoic acid from the previous step was lactonized by heating it under reflux in toluene for three hours with azeotropic removal of water. Upon cooling and standing, the pure trans-6-[2-[5-(4-fluorophenyl)-3-(1-methylethyl)-1-phenyl-1H-pyrazol-4-yl]ethyl]tetrahydro-4-hydroxy-2H-pyran-2-one, m.p. 163–165° C., crystallized from the solution. After recrystallization, the material melted at 165–167° C.

Analyzed for $C_{25}H_{27}FN_2O_3$: Calc. : C, 71.06%; H, 6.44%; N, 6.63% ; Found : C, 71.06%; H, 6.57%; N, 6.61% .

EXAMPLE 3

Preparation of trans-2-[2-[5-(4-fluorophenyl)-3-(1-methylethyl)-1-phenyl-1H-pyrazol-4-yl]ethenyl]-tetrahydro-4-hydroxy-2H-pyran-2-one

Step A—Preparation of 3-[5-(4-fluorophenyl)-3-(1-methylethyl)-1-phenyl-1H-pyrazol-4-yl]-2-propenoic acid, ethyl ester bis(Triphenylphosphine) palladium chloride (0.28 mmol) and ethyl acrylate (69.5 mmol) were dissolved in a mixture of 35 ml of anhydrous dimethylformamide and 35 ml of triethylamine. The solution was heated to 125° C., and 13.9 mmol of 4-bromo-5-(4-fluorophenyl)-3-(1-methylethyl)-1-phenyl-1H-pyrazole (prepared as described above in Step C of Example 2) was added in one portion.

The mixture was heated at 125° C., with stirring, for an additional two hours after which time an additional 0.78-mmol portion of the catalyst was added. This step of heating and addition of catalyst was repeated, after which the mixture was heated at 125° C. for an additional eighteen hours.

The mixture was cooled and partitioned between diethyl ether and water. The organic layer was separated, washed successively with 1 M hydrochloric acid, saturated sodium bicarbonate solution, and brine. The organic layer was dried over anhydrous magnesium sulfate, filtered, and evaporated to yield 4.1 g (77%) of 3-[5-(4-fluorophenyl)-3-(1-methylethyl)-1-phenyl-1H-pyrazol-4-yl]-2-propenoic acid, ethyl ester which was employed in the subsequent step without further purification.

Step B—Preparation of 2-[5-(4-fluorophenyl)-3-(1-methylethyl)-1-phenyl-1H-pyrazol-4-yl]-2-propen-1-ol 3-[5-(4-Fluorophenyl)-3-(1-methylethyl)-1-phenyl-1H-pyrazol-4-yl]-2-propenoic acid, ethyl ester (10.3 mmol) was dissolved in 35 ml of dichloromethane and the solution was cooled to 0° C. under a nitrogen atmosphere. To this cooled solution were added, dropwise with stirring, 11.3 mmol of a 1 M solution of diisobutyl aluminum in dichloromethane.

After addition was complete, the mixture was stirred for thirty minutes and then poured into ice-cold 2 M hydrochloric acid. This mixture was extracted twice with 50-ml portions of diethyl ether, and the combined ether extracts were washed successively with saturated sodium bicarbonate and brine and then dried over anhydrous magnesium sulfate.

The solvent was evaporated and the residue recrystallized to yield 2.8 g (98%) of 2-[5-(4-fluoro-phenyl)-3-(1-methylethyl)-1-phenyl-1H-pyrazol-4-yl]-2-propen-1-ol.

Step C—Preparation of 3-[5-(4-fluorophenyl)-3-(1-methylethyl)-1-phenyl-1H-pyrazol-4-yl]-2-propenal A mixture of 2-[5-(4-fluorophenyl)-3-(1-methylethyl)-1-phenyl-1H-pyrazol-4-yl]-2-propen-1-ol (6.9 mmol) and manganese dioxide (40 mmol) in 75 ml of chloroform was stirred at room temperature for two days. The mixture was filtered and concentrated to yield 2.2 g of 3-[5-(4-fluoro- phenyl)-3-(1-methylethyl)-1-phenyl-1H-pyrazol-4-yl]-2-propenal which was employed in the subsequent step without further purification.

Step D—Preparation of 7-[5-(4-fluorophenyl)-3-(1-methylethyl)-1-phenyl-1H-pyrazol-4-yl]-5-hydroxy-3-oxo-6-heptenoic acid, methyl ester Employing the procedure of Step E of Example 1, the 3-[5-(4-fluorophenyl)-3-(1-methylethyl)-1-phenyl-1H-pyrazol-4-yl]-2-propenal prepared in the previous step is converted to 7-[5-(4-fluorophenyl)-3-(1-methylethyl)-1-phenyl-1H-pyrazol-4-yl]-5-hydroxy-3-oxo-6-heptenoic acid, methyl ester.

Step E—Preparation of R*,R*-7-[5-(4-fluorophenyl)-3-(1-methylethyl)-1-phenyl-1H-pyrazol-4-yl]-β,δ-dihydroxy-6-heptenoic acid Employing the procedure of Step F of Example 1, the 7-[5-(4-fluorophenyl)-3-(1-methylethyl)-1-phenyl-1H-pyrazol-4-yl]-5-hydroxy-3-oxo-6-heptenoic acid, methyl ester prepared in the previous step is reduced to R*,R*-7-[5-(4-fluorophenyl)-3-(1-methylethyl)-1-phenyl-1H-pyrazol-4-yl]-β,δ-dihydroxy-6-heptenoic acid, methyl ester which is then saponified in dilute aqueous base and acidified to produce R*,R*-7-[5-(4-fluorophenyl)-3-(1-methylethyl)-1-phenyl-1H-pyrazol-4-yl]-β,δ-dihydroxy-6-heptenoic acid.

Step F—Preparation of trans-2-[2-[5-(4-fluorophenyl)-3-(1-methylethyl)-1-phenyl-1H H-pyrazol-4-yl]-ethenyl]tetrahydro-4-hydroxy-2H-pyran-2-one The R*,R*-7-[5-(4-fluorophenyl)-3-(1-methylethyl)-1-phenyl-1H-pyrazol-4-yl]-β,δ-dihydroxy-6-heptenoic acid prepared in the previous step is dissolved in dichloromethane and an equimolar amount of dicyclohexylcarbodiimide is added, together with a small amount of 4-dimethylaminopyridine as an acid scavenger. The mixture is cooled and allowed to stand for ten minutes. The mixture is concentrated and the residue is flash-chromatographed on silica gel to yield trans-2-[2-[5-(4-fluorophenyl)-3-(1-methylethyl)-1-phenyl-1H-pyrazol-4-yl]ethenyl]tetrahydro-4-hydroxy-2H-pyran-2-one.

EXAMPLE 4

Preparation of trans-2-[2-[1,5-bis(4-fluorophenyl)-3-(1-methylethyl)-1-phenyl-1H-pyrazol-4-yl]ethyl]-tetrahydro-4-hydroxy-2H-pyran-2-one Employing the method of Example 1, but substituting 4-fluorophenylhydrazine for the phenylhydrazine employed in Step C, there was obtained trans-2-[2-[1,5-bis-(4-fluorophenyl)-3-(1-methylethyl)-1-phenyl-1H-pyrazol-4-yl]-ethyl]tetrahydro-4-hydroxy-2H-pyran-2-one, m.p. 138–142° C.

The infrared spectrum (KBr pellet) of the product showed principal absorption peaks at 3400, 2962, 2871, 1710, 1564, 1454, 1377, 1225, 1159, 1052, and 971 cm$^{-1}$.

The 100 MHz proton magnetic resonance spectrum of a deuterochloroform solution of the product showed peaks at 1.3 (doublet, 6 protons), 1.6–1.9 (multiplet, 4 protons), 2.0 (broad singlet, 1 proton), 2.6–2.8 (multiplet, 4 protons), 3.0 (multiplet, 1 proton), 4.3 (multiplet, 1 proton), 4.6 (multiplet, 1 proton), and 6.9–7.2 (multiplet, 8 protons) parts per million downfield from the tetramethylsilane signal.

EXAMPLE 5

Preparation of trans-2-[2-[5-(4-fluorophenyl)-3-(1-methylethyl)-1-phenylmethyl-1H-pyrazol-4-yl]-ethyl]tetrahydro-4-hydroxy-2H-pyran-2-one Employing the method of Example 1, but substituting phenylmethylhydrazine for the hydrazine employed in Step C, there was obtained trans-2-[2-[5-(4-fluorophenyl)-3-(1-methylethyl)-1-phenylmethyl-1H-pyrazol-4-yl]ethyl]tetrahydro-4-hydroxy-2H-pyran-2-one, m.p. 145–148° C.

The infrared spectrum (KBr pellet) of the product showed principal absorption peaks at 3400, 2963, 2867, 1740, 1609, 1511, 1455, and 1226 cm$^{-1}$.

The 100 MHz proton magnetic resonance spectrum of a deuterochloroform solution of the product showed peaks at 1.3 (doublet, 6 protons), 1.6–1.8 (multiplet, 4 protons), 2.1 (broad singlet, 1 proton), 2.5–2.7 (multiplet, 4 protons), 3.0 (multiplet, 1 proton), 4.3 (multiplet, 1 proton), 4.6 (multiplet, 1 proton), 5.1 (singlet, 2 protons), and 6.9–7.3 (multiplet, 9 protons) parts per million downfield from the tetramethylsilane signal.

We claim:

1. A method of treating fungal infections in a mammal comprising administering to a mammal in need of such treatment an antifungally effective amount of a compound having the structural formula

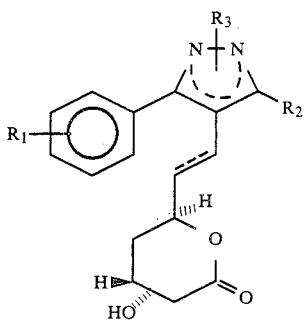

or a ring-opened $\beta,\delta$-dihydroxy acid of the formula

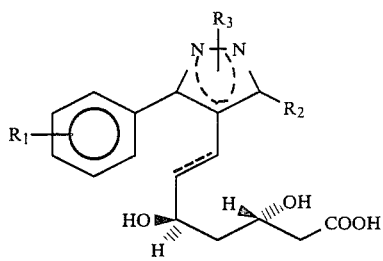

where the dashed lines indicate single or double bonds;
wherein $R_1$ is
 hydrogen; halogen; straight or branched lower alkyl; hydroxy; straight or branched lower alkyloxy; or straight or branched lower alkanoyl;
$R_2$ is
 straight or branched lower alkyl; or trifluoromethyl;
$R_3$ is
 phenyl;
 benzyl; or
 phenyl substituted with
  halogen,
  hydroxy,
  nitro,
  amino,
  straight or branched lower alkyl,
  straight or branched lower alkyloxy,
  methylsulfonyl, methylsulfinyl,
  acetamido, or
  benzoyl;
or a pharmaceutically acceptable salt thereof.

2. A method in accordance with claim 1 wherein said compound has the structural formula

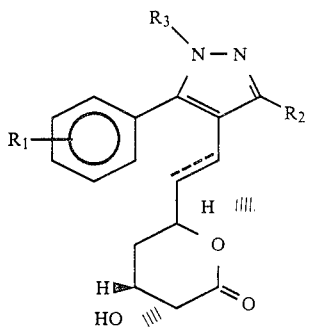

where ---- represents a single or double bond, and $R_1$, $R_2$, and $R_3$ are as defined therein.

3. A method in accordance with claim 1 wherein said compound has the structural formula

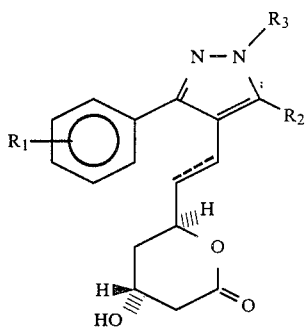

where ---- represents a single or double bond, and $R_1$, $R_2$, and $R_3$ are as defined therein.

4. A method in accordance with claim 1 wherein said compound is trans-6-[2-[5-(4-fluoro-phenyl)-3-(1-methylethyl)-1-phenyl-1H-pyrazol-4-yl]ethyl] tetrahydro-4-hydroxy-2H-pyran-2-one.

5. A method as defined in claim 1 wherein said compound is 5-(4-fluorophenyl)-$\beta,\delta$-dihydroxy-3-1-(methylethyl)-1-phenyl-1H-pyrazole-4-heptenoic acid, or a pharmaceutically acceptable salt thereof.

* * * * *